US009734691B2

(12) United States Patent
Parra et al.

(10) Patent No.: US 9,734,691 B2
(45) Date of Patent: Aug. 15, 2017

(54) PERSONALIZED WEARABLE GAS SENSOR USING BOTH THE AVERAGE AND THE RATE OF CHANGE OF THE GAS LEVEL

(71) Applicant: Intel Corporation, Santa Clara, CA (US)

(72) Inventors: Jeremy Parra, Beaverton, OR (US); Cynthia Lynn Merrill, Portland, OR (US)

(73) Assignee: Intel Corporation, Santa Clara, CA (US)

( * ) Notice: Subject to any disclaimer, the term of this patent is extended or adjusted under 35 U.S.C. 154(b) by 0 days.

(21) Appl. No.: 14/970,122

(22) Filed: Dec. 15, 2015

(65) Prior Publication Data

US 2017/0169692 A1    Jun. 15, 2017

(51) Int. Cl.
*G08B 21/00* (2006.01)
*G08B 21/14* (2006.01)
*G01N 33/00* (2006.01)

(52) U.S. Cl.
CPC .......... *G08B 21/14* (2013.01); *G01N 33/004* (2013.01)

(58) Field of Classification Search
CPC ...................................................... G08B 21/14
USPC ...... 340/539.1, 539.11, 573.1, 632, 633, 634
See application file for complete search history.

(56) References Cited

U.S. PATENT DOCUMENTS

| 6,433,696 | B1 | 8/2002 | Deiterman et al. |
| 6,914,534 | B2 | 7/2005 | Tanguay |
| 8,032,123 | B2 | 10/2011 | Sakhpara |
| 8,269,625 | B2 | 9/2012 | Hoy et al. |
| 2006/0125623 | A1 | 6/2006 | Appelt et al. |
| 2010/0217099 | A1 | 8/2010 | Leboeuf et al. |
| 2011/0298613 | A1* | 12/2011 | Ben Ayed .............. A61B 5/002 340/539.11 |

FOREIGN PATENT DOCUMENTS

| CA | 2211476 A1 | 1/1998 |
| KR | 1020110022254 A | 3/2011 |
| WO | WO-2015160830 A1 | 10/2015 |

OTHER PUBLICATIONS

"Carbon Monoxide In Workplace Atmospheres (Direct-Reading Monitor)", United States Department of Labor (Occupational Safety and Health Administration), [Online]. Retrieved from the Internet: <URL: https://www.osha.gov/dts/sltc/methods/inorganic/id209.html>, (Mar. 1993), 35 pgs.

(Continued)

*Primary Examiner* — Jeffery Hofsass
(74) *Attorney, Agent, or Firm* — Schwegman Lundberg & Woessner, P.A.

(57) ABSTRACT

Embodiments of a system and method for determining a personalized gas level exposure are generally described herein. A method may include receiving, at a wearable device, a plurality of gas level measurements for a gas level, determining, using the plurality of gas level measurements, a five-minute average gas level, in response to determining that the five-minute average gas level exceeds an instantaneous exposure threshold, issuing a dangerous exposure alert at the wearable device, determining, from the plurality of gas level measurements, a rate of change for the gas level, and in response to determining that the rate of change indicates the gas level is decreasing, disabling the dangerous exposure alert.

23 Claims, 7 Drawing Sheets

(56) References Cited

OTHER PUBLICATIONS

"How was Nest Protect certified?", Nest Support, [Online]. Retrieved from the Internet: <URL: https://nest.com/support/article/How-was-Nest-Protect-certified, (Last Updated: Jun. 17, 2015), 2 pgs.
"International Application Serial No. PCT/US2016/060809, International Search Report mailes Jan. 20, 2017", 4 pgs.
"International Application Serial No. PCT/US2016/060809, Written Opinion mailed Jan. 20, 2017", 7 pgs.
"Which CO Detector is right for You?", Carbon Monoxide Detector HQ, [Online]. Retrieved from the Internet: <URL: http://www.carbonmonoxidedetectorhq.com/carbon-monoxide-levels-standards/>, (Accessed: Nov. 9, 2016), 5 pgs.

\* cited by examiner

PERSONALIZED WEARABLE GAS SENSOR USING BOTH THE AVERAGE AND THE RATE OF CHANGE OF THE GAS LEVEL

BACKGROUND

According to some technical analysts, there will be over 50 billion connected "things" by the year 2020. This will completely transform current infrastructures and will drive new innovations in industry, products, and services. Internet-of-Things (IoT) is term that represents devices and systems that communicate over a network, such as the internet. The devices and systems may include sensors.

Exposure to certain gasses is detrimental to human health. Depending on the level and duration of exposure, significant health effects may be incurred, up to and including death. Exposure to these gasses occurs when individuals are in proximity to sources of the gas. Sensors are used to measure gas concentrations.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
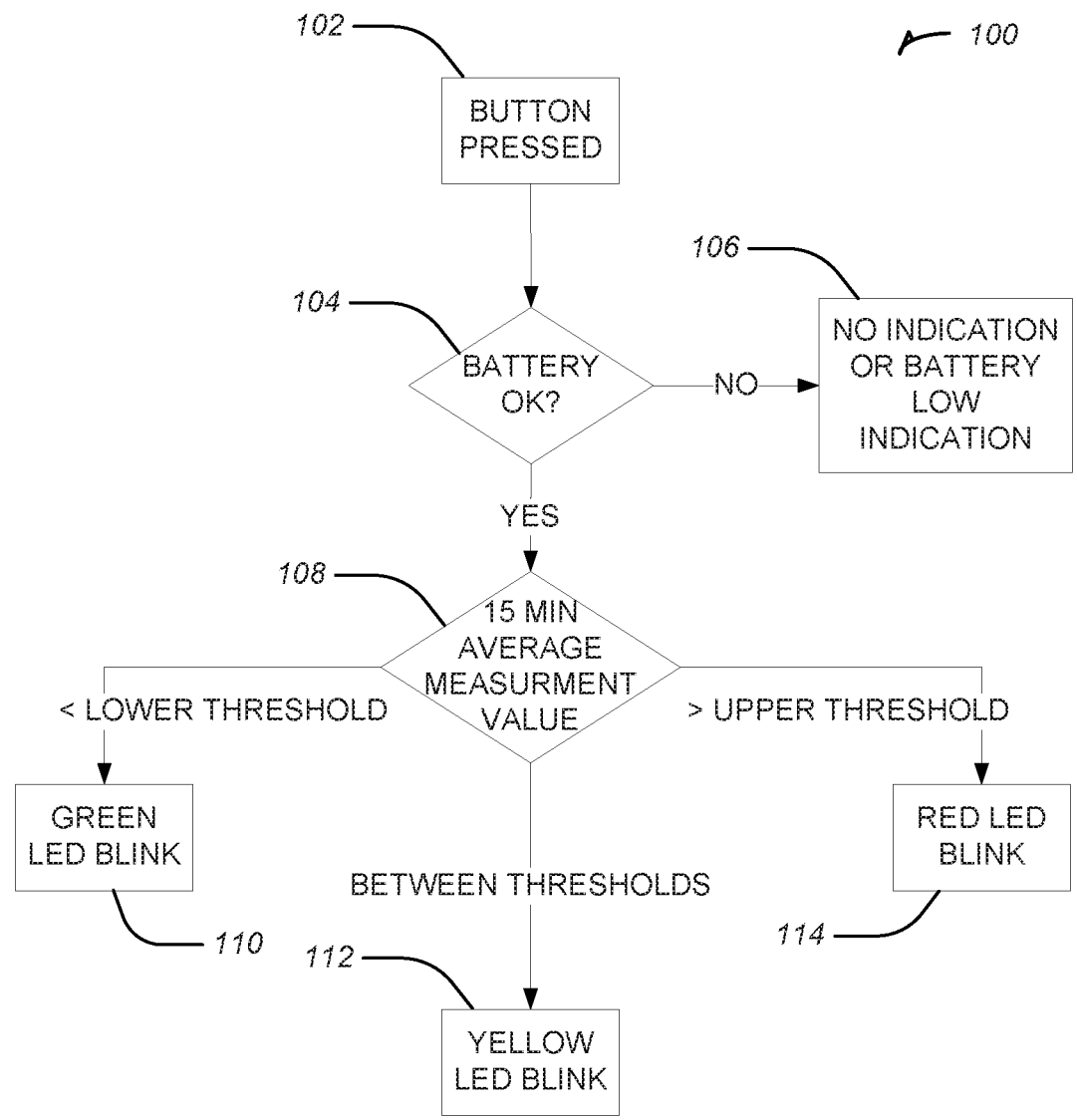
FIG. 1 illustrates a user initiated gas level update process flow in accordance with some embodiments.

Internet-of-Things (IoT) devices, such as wearable devices, and mobile devices, such as mobile phones, are increasingly being used to deliver personalized data to users. One type of wearable device may measure a local gas level for a user. The gas level may be a personalized gas level when the wearable device is worn by a user over time. A wearable device may measure one gas or a plurality of gasses, and may have other uses as well, such as a heart rate monitor, watch, etc. The wearable monitor described in various embodiments below details a carbon monoxide (CO) gas monitor. Other gasses may be monitored by a wearable monitor, such as carbon dioxide, natural gas, or the like.

Carbon monoxide (CO) is a colorless, odorless, and tasteless gas that is slightly less dense than air. CO is one type of dangerous gas that may be detrimental to the health of humans. For example, depending on the level and duration of CO exposure, significant health effects may be experienced, including death. Exposure to CO may occur when individuals are in proximity to CO sources, such as combustion appliances, open fires, automobiles, etc.

Limiting long term exposure to low levels of CO may have significant positive impacts on human health, including reduced carboxyhemoglobin levels, reduced impacts to cardiovascular tissue, and reduced negative impact on birth weight. Instantaneous exposure (e.g., around one to fifteen minutes) to high levels of CO may be deadly.

Many embodiments of sensors may be used to measure CO. Simple devices exist for alerting a user of the presence of CO based on a binary logic scheme (e.g., when a single value is exceeded for a specified average interval, a tone is sounded). Other continuous monitoring systems exist that provide continuous CO concentration measurements that may be read and understood by properly trained users.

These example systems fail to provide more than the single function of binary alerting or use complicated mechanisms that need trained users. A simplified communication system for continuous CO measurements is described below. The notification scheme addresses multiple dimensions of user exposure and may include one or more of the following: (1) warning a user of extreme exposure events, (2) providing useful feedback to a user action that may mitigate or exacerbate the user's exposure to CO, (3) giving information about the long term exposure of the user to CO, (4) incorporating the scientific recommendations for limiting CO exposure, and (5) working within the confines of a simple user interface.

The logic scheme and user interface described below may be used in a CO sensing embodiment, such as a wearable CO sensing embodiment. The logic scheme and user interface may provide alerts and information to the user based on recommended level thresholds through a simple and intuitive user interface.

In an example, a wearable device may include visual or auditory alerting of instantaneous exposure (e.g., a one to fifteen minute average) to high levels of carbon monoxide, visual or auditory alerting of acute exposure (e.g., a fifteen minute to eight hour average) to levels of carbon monoxide that exceed recommended levels, or visual or auditory alerting of long term or chronic exposure (e.g., a twelve-hour to twenty-four-hour average) that exceed recommended levels.

In an example, a wearable device may provide simple and robust feedback to a user to indicate the efficacy of user actions taken to lower CO exposure. In another example a wearable device may provide a logical scheme for keeping track of exceedance of recommended guideline levels as well as a simplified notification scheme for communicating this information to an untrained user. For example, a wearable device may indicate to a user the efficacy of actions taken by the user after the user has been alerted to a heightened level of CO in the user's proximity.

Some devices exist that provide a binary alerting for instantaneous exposure (e.g., a one to fifteen minute average) to high levels of CO, such as sounding an alert when an average CO level exceeds 70 parts per million (ppm). Because these devices are stationary (e.g., in a home or office building) and because they cannot keep track of the changes in CO concentration in a user's immediate vicinity, these devices are unable to provide relevant feedback to the user if and when the user has taken action to mitigate the user's personal exposure to CO (e.g., by going outside or otherwise vacating the premises). The wearable devices described herein provide an initial alert to elevated CO levels and may give detailed instructions or feedback to a user based on changes in CO levels as measured by a CO sensor on the wearable device. Other stationary devices exist to continuously monitor CO. These devices may be used to calculate various averages of CO (e.g., fifteen minute, one hour, eight hour, and twenty-four hour) to be compared to exposure standards. The computation and tracking of these averages for current devices is usually performed by trained personal and are not obvious for untrained end users.

The wearable devices described herein provide the CO average and count the number of exceedances in a given period to effectively and simply inform a user about the exceedance of CO exposure standards.

In an example, a wearable device may provide a logical scheme for tracking exceedances of recommended exposure levels. Air quality standards for CO are developed by reviewing epidemiological studies and are issued, published, or endorsed by regulatory and advisory institutions. For example, the Environmental Protection Agency (EPA) in the United States issues National Ambient Air Quality Standards (NAAQS) that include CO guidelines. The World Health Organization (WHO) also puts out recommendations for limiting acute and chronic exposure to CO. The wearable devices discussed herein may be based on WHO guidelines for CO exposure limits, such as WHO Guidelines for Indoor Air Quality: Selected Pollutants, 2010, WHO, ISBN 978 92 890 0213 4. Other guidelines from other organizations may be used with the wearable devices to alert a user about unsafe CO levels.

In an example, four use cases may be implemented individually or in combination in a wearable device. The first use case includes providing a user with a user interface that allows for the user to easily and simply ascertain a current relative level of CO for the user. The second use case includes providing a user with an alert immediately and continuously when CO levels reach above a threshold where death may occur from exposure to CO. The third use case includes alerting a user when the recommended CO levels for maintaining wellbeing are exceeded, and providing the user with prompts that are dynamically updated based on the measured changes in CO concentration. The fourth use case includes providing a user with information regarding exceedance of a long term or chronic CO exposure.

FIG. 1 illustrates a user initiated gas level update process flow 100 in accordance with some embodiments. In an example, FIG. 1 corresponds to the first use case introduced above to allow a user to ascertain a current CO level at a wearable device. In an example, a user may find out what the current CO level is by initiating an interaction with the device. In an example wearable device, a user may press a hardware button, the wearable device may receive an indication that the button is pressed 102, and the device may respond based on a function of fifteen-minute averages of recent CO measurements at block 108. The wearable device may include a battery. The wearable device may determine at block 104, whether the battery is currently functioning, for example, has more than 5% power, or has any power. When the battery is functioning, the process flow 100 may move to block 108. When the battery is not functioning or is low, the wearable device may indicate, at block 106, that the battery is low or may not do anything if the battery is completely drained.

In an example, at block 108, the wearable device may determine a fifteen minute average measurement value for the previous fifteen minutes' worth of CO measurements. A single CO measurement value may be susceptible to false positives or false negatives and may not be as reliable as an average measurement value. The fifteen minute average measurement value from block 108 may be compared to various thresholds on a range to determine an output. For example, a lower threshold and an upper threshold may be defined. When the fifteen minute average measurement value exceeds the lower threshold, it may indicate the start of a potential issue for unsafe gas levels. When the fifteen minute average measurement value exceeds the upper threshold, it may indicate a potentially serious issue or a developing serious unsafe gas level. In an example, the lower threshold and upper threshold may be determined from standards. For example, the lower threshold may include 57 ppm of CO gas and the upper threshold may include 73 ppm of CO gas.

The fifteen minute average measurement value compared to the two thresholds may trigger activity, such as an alert, at the wearable device. For example, when the fifteen minute average measurement value is less than 57 ppm, the wearable device may cause an LED to blink green at block 110, indicating that the current air is acceptable. When the fifteen minute average measurement value is between 57 and 73 ppm, the wearable device may cause an LED to blink yellow at block 112, indicating that the current air is potentially harmful. When the fifteen minute average measurement value is above 73, the wearable device may cause an LED to blink red at block 114, indicating that the current air is harmful. Other alerts may include audible warnings or statements, haptic feedback, written warnings or picture warnings displayed on a user interface, or the like. In another example, different thresholds (e.g., 50 ppm and 80 ppm) or different numbers of thresholds (e.g., three, four, five, etc.) may be used. For different numbers of thresholds, additional alerts for different ranges may be used, such as below a first threshold, between the first and a second threshold, between the second and a third threshold, and above the third threshold. In yet another example, the fifteen minute average measurement value may include a weighting factor, and an alert may include an indication that a CO gas level at the wearable device is increasing or decreasing, in addition to, or instead of, the alerts described above.

Figure 2:
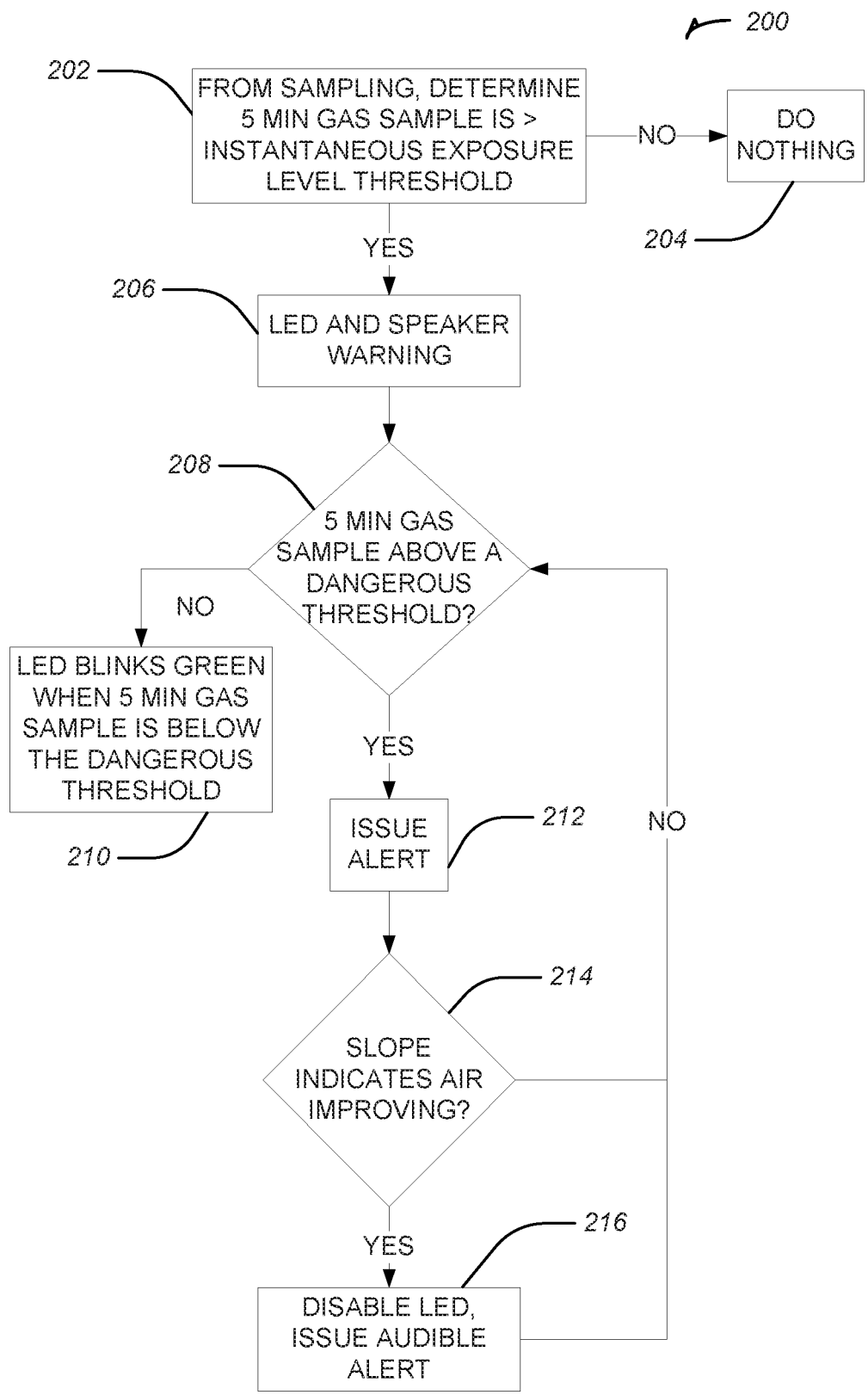
FIG. 2 illustrates an instantaneous exposure level warning process flow in accordance with some embodiments.

FIG. 2 illustrates an instantaneous exposure level warning process flow 200 in accordance with some embodiments. In an example, FIG. 2 corresponds to the second use case introduced above to alert a user to an instantaneous exposure at a wearable device. In an example wearable device, the process flow 200 may be used to alert a user to a personalized instantaneous exposure alert for a dangerous gas exposure, such as CO. The wearable device may continuously monitor a five-minute average of recent CO measurements at block 202. The wearable device may determine, at block 202, if the five-minute average of recent CO measurements exceeds an instantaneous exposure threshold. The instantaneous exposure threshold may be predetermined, such as from a standard, to be 200 ppm. When the five-minute average of recent CO measurements falls below the instantaneous exposure threshold, the wearable device may do nothing at block 204, and continue to monitor the gas level. When the five-minute average of recent CO measurements exceeds the instantaneous exposure threshold, the wearable device may alert the user to the very dangerous CO level, such as with a visible, audible, or haptic alert at block 206. For example, the alert may include a fast blinking red LED. Process flow 200 may run autonomously in the background (i.e., without user intervention) to automatically detect instantaneous exposure to a dangerous CO level.

The wearable device may determine whether the CO level continues to exceed the instantaneous exposure threshold at block 208. When the CO level no longer exceeds the instantaneous exposure threshold, the wearable device may indicate to the user that the air is clear at block 210. For example, the wearable device may blink a green LED when the five-minute average of recent CO measurements is below the instantaneous exposure threshold. When the CO level continues to exceed the instantaneous exposure threshold, the wearable device may issue an alert at block 212. The alert at block 212 may be, for example, a warning that continued exposure to the current CO level may result in death. After the alert at block 212 is issued, the wearable device may determine from a slope of a plurality of five-minute averages of recent CO measurements whether the air is improving (i.e., the CO level is decreasing), or not improving (i.e., the CO level is increasing or staying the same) at block 214. In an example, the slope may be compared to a slope threshold, such as −16 ppm/minute to determine if the slope indicates the air is sufficiently improving. When the air is improving, the wearable device may disable an active LED or issue an audible alert, such as a notification indicating that the air is improving at block 216. Even though the air is improving, the CO level may still be at a dangerous level, so after block 216, the process flow may iterate at block 208.

When the air is not improving, the wearable device may add an auditory alert to the visual alert (e.g., red LED). The auditory alert may be in the form of loud beeps or a voice warning to get to better air immediately. The process flow 200 may iterate when the air is not improving, at block 208. As long as the five-minute average of recent CO measurements remains above a 200 ppm, the wearable device may continue to issue an alert. In an example, every five minutes, the wearable device may re-check the five-minute average of recent CO measurements to determine whether the absolute level has decreased or whether the slope indicates the air is improving. If the slope is staying the same or increasing, this may indicate that the user of the wearable device is not getting to clean air fast enough. The wearable device may continue blinking a red LED, sounding loud beeps, or emitting a voice warning when the air is not improving. If the slope is decreasing, this may indicate that the user has moved to cleaner air. The wearable device may play a voice message acknowledging this improvement, such as for three minutes. The wearable device may disable the red LED. If the five-minute average of recent CO measurements (e.g., the absolute value) decreases below 200 ppm, this may indicate that the user has been in cleaner air for a while. The wearable device may play a pleasant chime to indicate this, and may exit the instantaneous exposure alert process flow 200.

Figure 3:
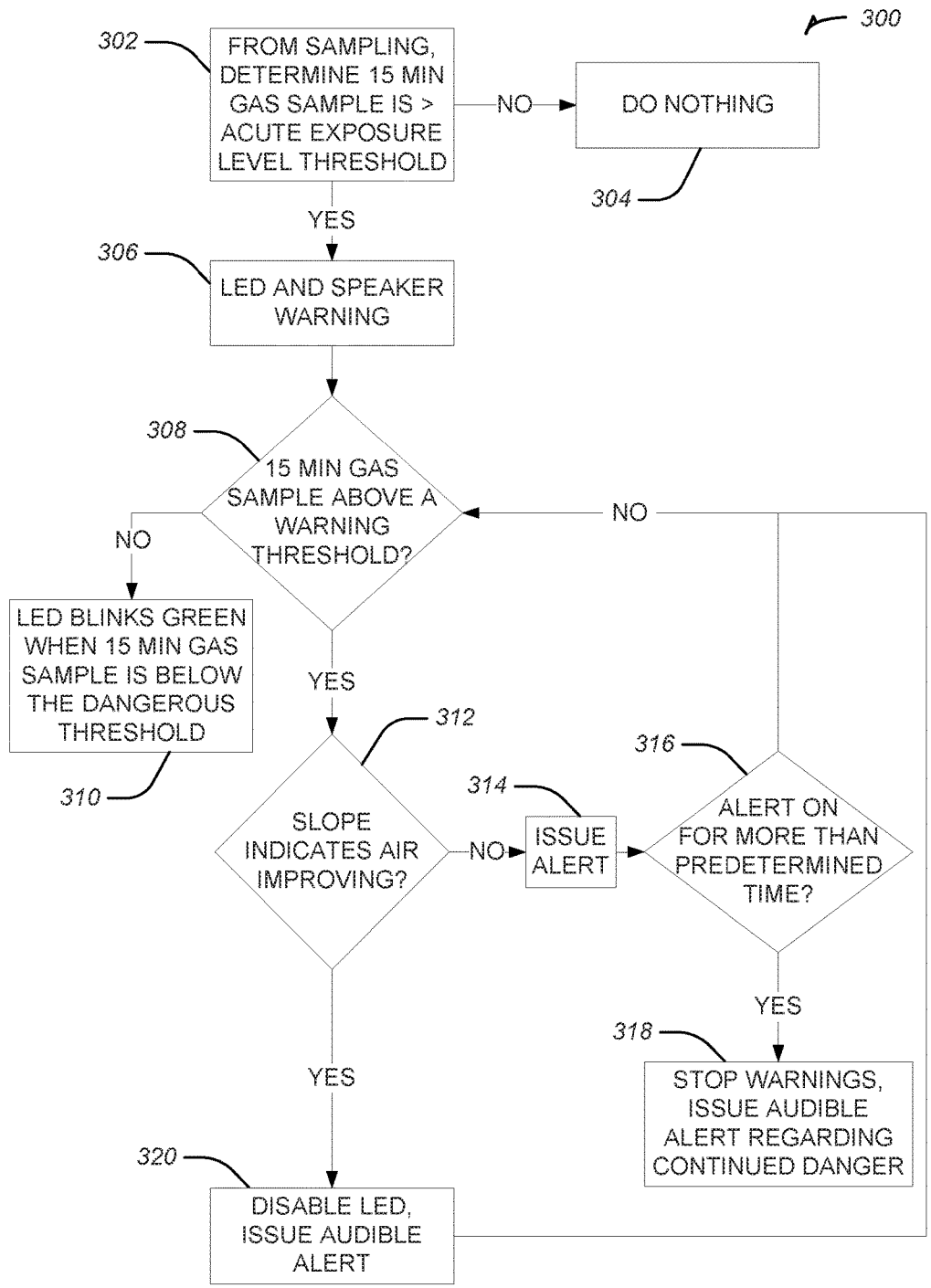
FIG. 3 illustrates an acute exposure level warning process flow in accordance with some embodiments.

FIG. 3 illustrates an acute exposure level warning process flow 300 in accordance with some embodiments. In an example, FIG. 3 corresponds to the third use case introduced above to alert a user to an acute exposure. In an example wearable device, the process flow 300 may be used to alert a user to a personalized acute exposure alert. The wearable device may continuously monitor a fifteen-minute average of recent CO measurements to determine whether the fifteen-minute average of recent CO measurements exceeds the acute exposure threshold at block 302. When the fifteen-minute average of recent CO measurements exceeds an acute exposure threshold, the wearable device may alert the user at block 306. When the fifteen-minute average of recent CO measurements falls below the threshold, the process flow 300 may include doing nothing at block 304. The process flow 300 may then be repeated fifteen minutes later. Process flow 300 may run autonomously in the background (i.e., without user intervention) to automatically detect acute exposure to a potentially dangerous CO level.

The acute exposure threshold may be predetermined from a standard, and may include 57 ppm CO gas, in an example. The wearable device may record a new exceedance when the acute exposure threshold is exceeded by the fifteen-minute average of recent CO measurements. The wearable device may alert the user to the acute exposure threshold exceedance as a moderate CO level present in the user's air environment. For example, block 306 may include a slow blinking yellow LED.

In an example, the process flow 300 may include determining, at block 308 if the fifteen-minute average of recent CO measurements continues to exceed the acute exposure threshold. When the CO level no longer exceeds the acute exposure threshold, the wearable device may indicate to the user that the air is clear at block 310. For example, the wearable device may blink a green LED when the fifteen-minute average of recent CO measurements is below the acute exposure threshold.

When the fifteen-minute average of recent CO measurements exceeds the acute exposure threshold, the wearable device may determine, from a slope of a plurality of fifteen-minute averages of recent CO measurements, that the air is improving (i.e., the CO level is decreasing), or the air is not improving (i.e., the CO level is increasing or staying the same) at block 312. In an example, the slope may be compared to a slope threshold, such as −14 ppm/minute to determine if the slope indicates the air is sufficiently improving. When the air is improving, the wearable device may disable an active LED or issue an audible alert, such as a notification indicating that the air is improving at block 320. Even though the air is improving, the CO level may still be at a problematic level, so after block 320, the process flow may iterate at block 308.

When the air is not improving, the wearable device may issue an auditory alert or a visual alert (e.g., the yellow LED) at block 314. The auditory alert may be in the form of beeps or a voice warning that the air is still bad. The process flow 300 may iterate when the air is not improving, at block 308. Before iterating at block 308, the wearable device may determine if the alert of block 314 has been on for more than a predetermined amount of time (e.g., 20 minutes) at block 316. For example, block 316 may include determining whether the alert of block 314 was first issued more than the predetermined amount of time before a current time. In another example, block 316 may include determining whether the alert of block 314 has issued more than a predetermined number of times (e.g., issue the alert at block 314, then determine how many times the alert has been issued, and if it exceeds the predetermined number of times, for example, five times).

As long as the fifteen-minute average of recent CO measurements remains above the acute exposure threshold, the wearable device may continue to issue an alert, until the alert is on for more than the predetermined amount of time. If the alert is on for more than the predetermined amount of time, the process flow may include stopping the warnings at block 318. Block 318 may include issuing an audible alert or visual alert regarding the continued danger. Block 318 may indicate that the alert is shutting off, such as to conserve battery. In an example, the predetermined amount of time may be user configurable.

In an example, every fifteen minutes, the wearable device may re-check the fifteen-minute average of recent CO measurements to determine whether the absolute level has decreased or whether the slope indicates the air is improving. If the slope is staying the same or increasing, this may indicate that the user of the wearable device is not getting to clean air fast enough. The wearable device may continue the yellow blinking of an LED, loud beeps, or a voice warning when the air is not improving.

If after fifteen minutes, the wearable device determines that the CO level is staying the same or increasing (e.g., by measuring the slope), the wearable device may change the visual alert, such as changing a yellow blinking LED to a red blinking LED. The wearable device may play a voice warning about the bad air.

If the slope is decreasing, this may indicate that the user has moved to cleaner air, such as by visual, audible, or haptic feedback. The wearable device may play a voice message or chimes acknowledging this improvement, such as one to two chime tones. The wearable device may disable the red LED. If the fifteen-minute average of recent CO measurements (e.g., the absolute value) decreases below 57 ppm, this may also be used to indicate that the user has been in cleaner air for a while. The wearable device may play a pleasant chime to indicate this, and may exit the acute exposure alert process flow 300.

Figure 4:
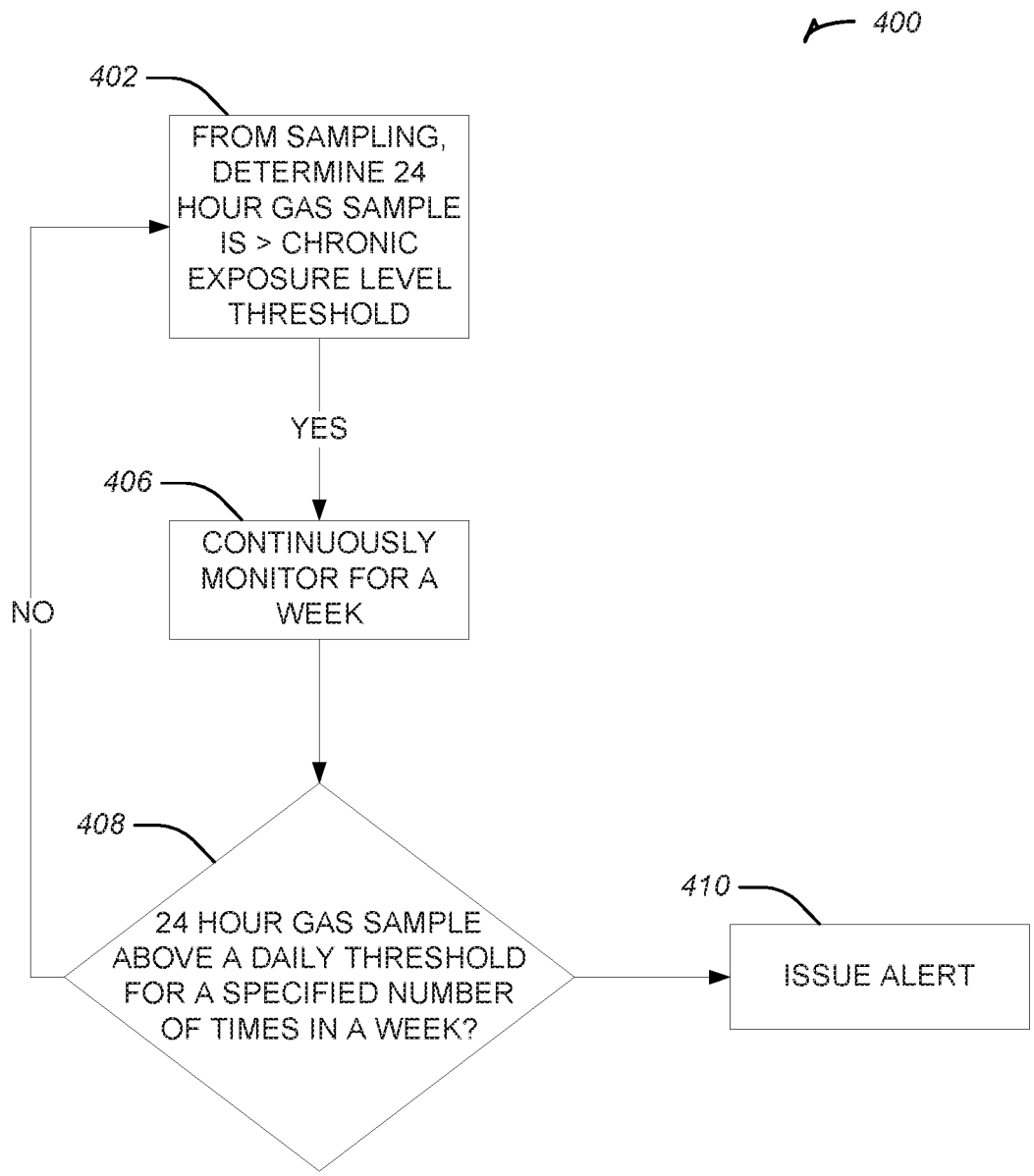
FIG. 4 illustrates a chronic exposure level warning process flow in accordance with some embodiments.

FIG. 4 illustrates a chronic exposure level warning process flow 400 in accordance with some embodiments. In an example, FIG. 4 corresponds to the fourth use case introduced above to alert a user to a chronic exposure. In an example wearable device, the process flow 400 may be used to alert a user to a personalized chronic exposure alert. The wearable device may monitor a twenty-four-hour average of recent CO measurements at block 402. The wearable device may determine whether the chronic exposure threshold is exceeded by the twenty-four-hour average of recent CO measurements, such as at a predetermined time each day. For example, at 3:00 AM each day, the wearable device may determine whether the twenty-four-hour average of recent CO measurements, exceeds the chronic exposure threshold. In an example, the chronic exposure threshold may be determined from a standard. The chronic exposure threshold may include 5.17 ppm CO gas. The wearable device may log the number of times the twenty-four-hour average of recent CO measurements exceeds the chronic exposure threshold at block 406. The wearable device may determine, if in the past seven days, for example, there are any incidents of the twenty-four-hour average of recent CO measurements exceeding the chronic exposure threshold at block 408. If the incidents occurred more than a specified number of times (e.g., three days out of the previous seven), the process flow 400 may include issuing an alert at block 410. The alert at block 410 may include an indication that levels of CO gas were higher than usual or that the CO gas levels may become problematic. If the incidents occurred fewer than the specified number of times, the wearable device may do nothing or may indicate that the air was clear for the previous week. The process flow 400 may be iterated at block 402, such as each day at a given time. Process flow 400 may run autonomously in the background (i.e., without user intervention) to automatically detect chronic exposure to a potentially dangerous CO level.

The above use cases may be used separately or combined in any way. For example, a wearable device may issue an acute exposure alert for a CO level above an acute exposure threshold using a fifteen-minute average of recent CO measurements. Five minutes later, the CO level determined from a five-minute average of recent CO measurements may exceed an instantaneous exposure threshold, and the wearable device may issue an instantaneous exposure alert. In another example, a user may press a hardware button on a wearable device to receive a current CO level status. If the status indicates that the CO level exceeds an upper threshold, the wearable device may indicate such, and then initiate an acute exposure alert if a fifteen-minute average of recent CO measurements exceeds an acute exposure threshold. In yet another example, a wearable device may determine that a chronic exposure threshold has been exceeded more than a specified number of times in a week. A user may then press a hardware button on the wearable device to receive a current CO level status. The current CO level status may indicate that the current CO level is below a lower threshold and safe. This may provide the user with peace of mind as well as allowing a user to attempt to determine, but pressing the hardware button at various places or times during a day, where the increased CO levels exist.

Figure 5:
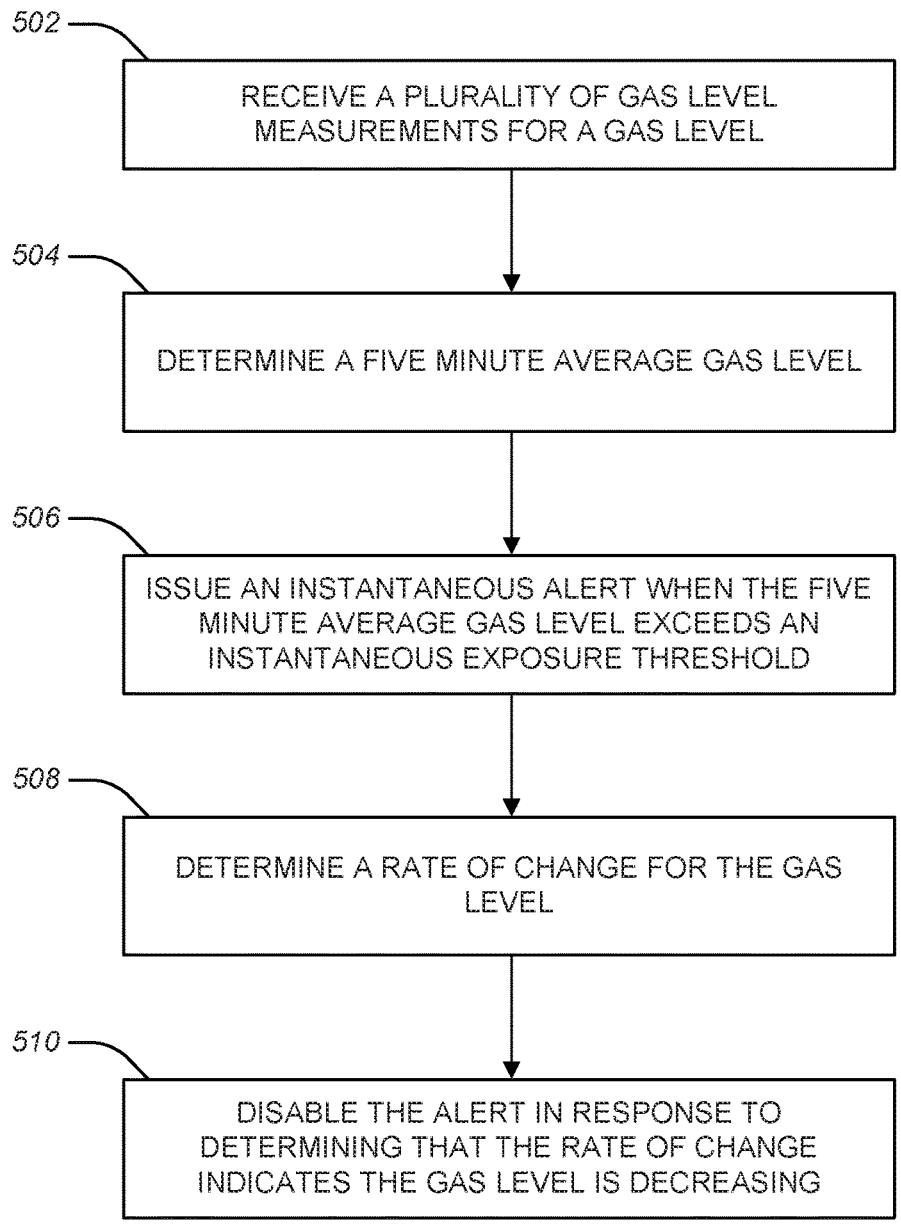
FIG. 5 illustrates a flowchart showing a technique for determining a personalized gas level exposure in accordance with some embodiments.

FIG. 5 illustrates a flowchart showing a technique 500 for determining a personalized gas level exposure in accordance with some embodiments. The technique 500 includes an operation 502 to receive a plurality of gas level measurements for a gas level. The plurality of gas level measurements may be made by a sensor of the wearable device. In an example, the gas level is a level of CO gas.

The technique 500 includes an operation 504 to determine a five-minute average gas level. The technique 500 includes an operation 506 to issue an instantaneous alert when the five-minute average gas level exceeds an instantaneous exposure threshold. In response to determining that the five-minute average gas level falls below the instantaneous exposure threshold, the technique 500 may include indicating the gas level is at a safe level. The technique 500 includes an operation 508 to determine a rate of change for the gas level. The technique 500 includes an operation 510 to disable the alert in response to determining that the rate of change indicates the gas level is decreasing. In an example, the rate of change indicates that the gas level is decreasing when the rate of change is negative and exceeds a slope threshold.

The technique 500 may include an operation to determine, using the plurality of gas level measurements, a fifteen-minute average gas level. The operation may include, in response to determining that the fifteen-minute average gas level exceeds an acute exposure threshold, issuing an acute alert at the wearable device. In an example, the technique 500 may include, when the five-minute average gas level exceeds the instantaneous exposure threshold, and the fifteen-minute average gas level exceeds the acute exposure threshold, issuing the instantaneous alert and not the acute alert. The technique 500 may include disabling the acute alert when iterating the operation results in the fifteen-minute average gas level exceeding the acute exposure threshold for 20 minutes.

The technique 500 may include an operation to determine, using the plurality of gas level measurements, a set of twenty-four-hour average gas levels. The operation may include, in response to determining that a minimum number of the set of twenty-four-hour average gas levels exceed a daily exposure threshold, issuing a chronic exposure alert at the wearable device. In an example, the set of twenty-four-hour average gas levels includes seven twenty-four-hour average gas levels and the minimum number is three.

The technique 500 may include an operation to, in response to a hardware button being pressed, determine, using the plurality of gas level measurements, a fifteen-minute average gas level. The operation may include determining where the fifteen-minute average gas level falls within a range. In an example, the operation includes, when the fifteen-minute average gas level falls in a lowest section of the range, indicating the gas level is at a safe level. In an example, the operation includes, when the fifteen-minute average gas level falls in a middle section of the range, issuing a moderate gas level alert. In an example, the operation includes, when the fifteen-minute average gas level falls in a highest section of the range, issuing a high gas level alert. The minimum value of the highest section of the range may be lower than the instantaneous exposure threshold.

Figure 6:
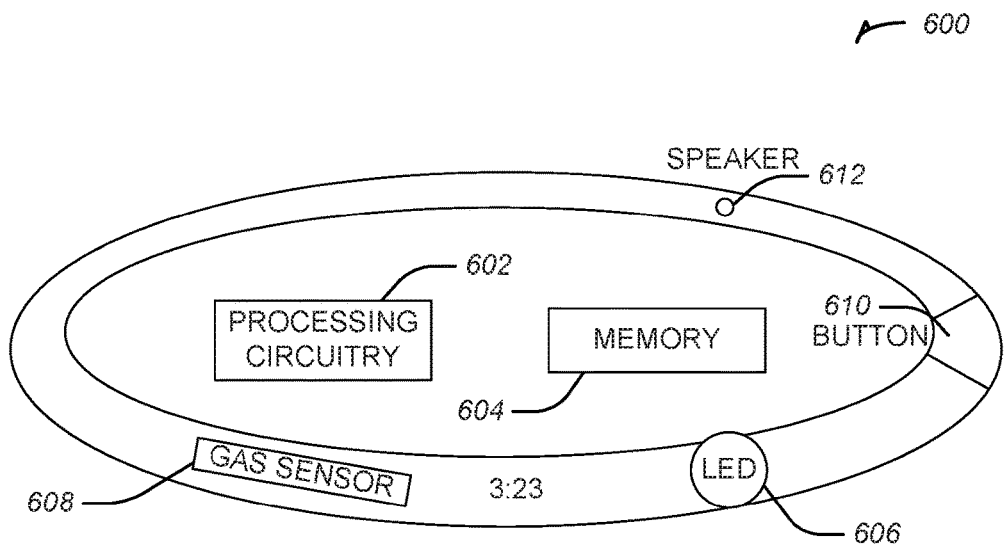
FIG. 6 illustrates a wearable device including a gas sensor in accordance with some embodiments.

FIG. 6 illustrates a wearable device 600 including a gas sensor 608 in accordance with some embodiments. The wearable device 600 may include processing circuitry 602 and memory 604. In an example, the wearable device 600 includes an LED 606. The LED 606 may include a plurality of LEDs, such as a green LED, a yellow LED, and a red LED for alerting a user. The gas sensor 608 may take measurements of a gas level, which may be stored on the memory 604. The processing circuitry 602 may determine a five-minute average, a fifteen-minute average, or a twenty-four-hour average of recent gas level measurements taken by the gas sensor 608. The processing circuitry 602 may be used to perform the process flows 100-400 described above. The wearable device 600 may include a hardware button 610 that may be pressed by a user to initiate the user initiated gas level update process flow 100. The wearable device 600 may include a speaker 612 to issue audible alerts to a user.

Figure 7:
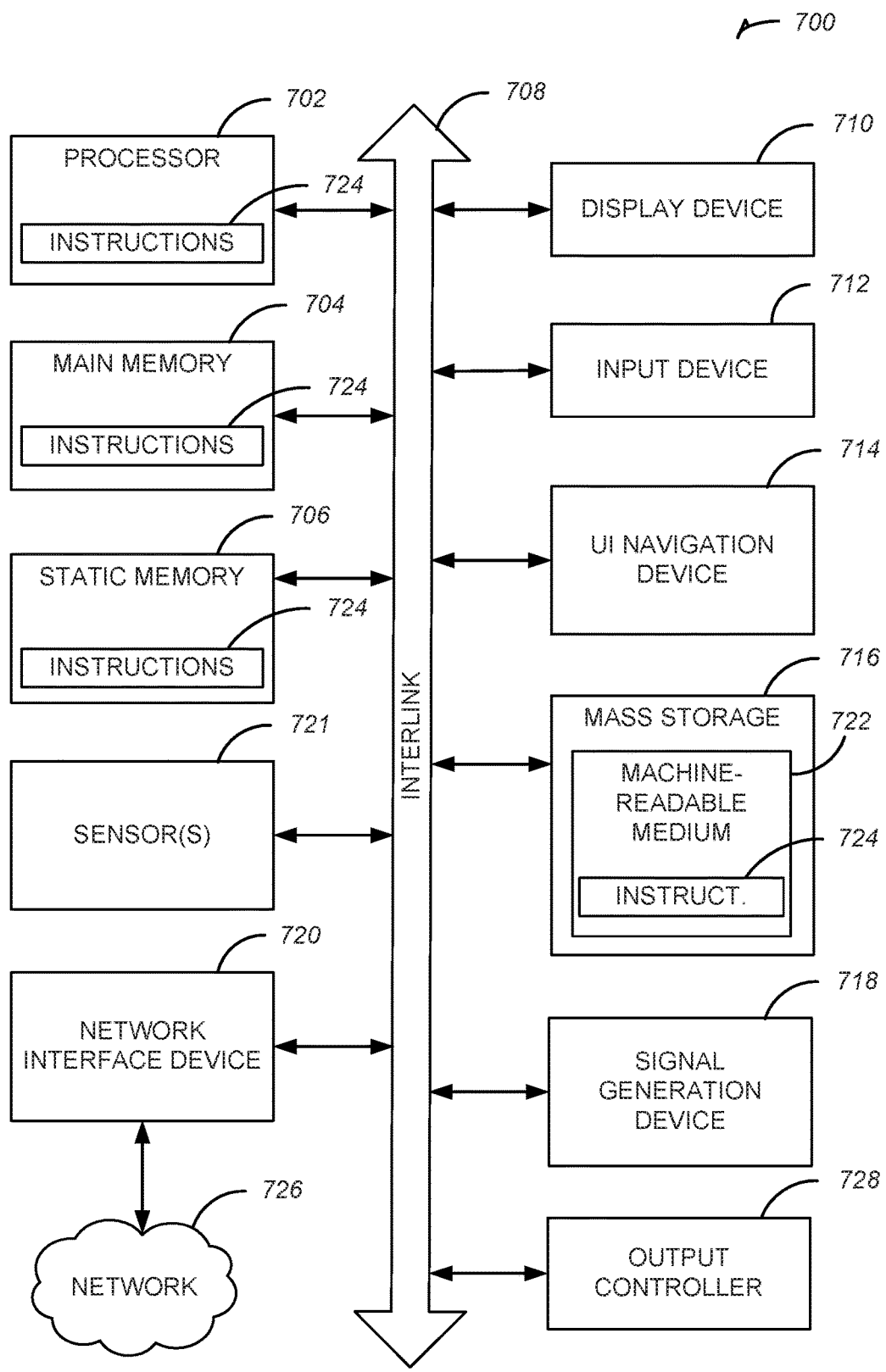
FIG. 7 illustrates generally an example of a block diagram of a machine upon which any one or more of the techniques (e.g., methodologies) discussed herein may perform in accordance with some embodiments.

FIG. 7 illustrates generally an example of a block diagram of a machine 700 upon which any one or more of the techniques (e.g., methodologies) discussed herein may perform in accordance with some embodiments. In alternative embodiments, the machine 700 may operate as a standalone device or may be connected (e.g., networked) to other machines. In a networked deployment, the machine 700 may operate in the capacity of a server machine, a client machine, or both in server-client network environments. In an example, the machine 700 may act as a peer machine in peer-to-peer (P2P) (or other distributed) network environment. The machine 700 may be a wearable device, a personal digital assistant (PDA), a mobile telephone, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate on, logic or a number of components, modules, or mechanisms. Modules are tangible entities (e.g., hardware) capable of performing specified operations when operating. A module includes hardware. In an example, the hardware may be specifically configured to carry out a specific operation (e.g., hardwired). In an example, the hardware may include configurable execution units (e.g., transistors, circuits, etc.) and a computer readable medium containing instructions, where the instructions configure the execution units to carry out a specific operation when in operation. The configuring may occur under the direction of the executions units or a loading mechanism. Accordingly, the execution units are communicatively coupled to the computer readable medium when the device is operating. In this example, the execution units may be a member of more than one module. For example, under operation, the execution units may be configured by a first set of instructions to implement a first module at one point in time and reconfigured by a second set of instructions to implement a second module.

Machine (e.g., computer system) 700 may include a hardware processor 702 (e.g., a central processing unit (CPU), a graphics processing unit (GPU), a hardware processor core, or any combination thereof), a main memory 704 and a static memory 706, some or all of which may communicate with each other via an interlink (e.g., bus) 708. The machine 700 may further include a display unit 710, an alphanumeric input device 712 (e.g., a keyboard), and a user interface (UI) navigation device 714 (e.g., a mouse). In an example, the display unit 710, alphanumeric input device 712 and UI navigation device 714 may be a touch screen display. The machine 700 may additionally include a storage device (e.g., drive unit) 716, a signal generation device 718 (e.g., a speaker), a network interface device 720, and one or more sensors 721, such as a global positioning system (GPS) sensor, compass, accelerometer, or other sensor. The machine 700 may include an output controller 728, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

The storage device 716 may include a machine readable medium 722 that is non-transitory on which is stored one or more sets of data structures or instructions 724 (e.g., software) embodying or utilized by any one or more of the techniques or functions described herein. The instructions 724 may also reside, completely or at least partially, within the main memory 704, within static memory 706, or within the hardware processor 702 during execution thereof by the machine 700. In an example, one or any combination of the hardware processor 702, the main memory 704, the static memory 706, or the storage device 716 may constitute machine readable media.

While the machine readable medium 722 is illustrated as a single medium, the term "machine readable medium" may include a single medium or multiple media (e.g., a centralized or distributed database, and/or associated caches and servers) configured to store the one or more instructions 724.

The term "machine readable medium" may include any medium that is capable of storing, encoding, or carrying instructions for execution by the machine 700 and that cause the machine 700 to perform any one or more of the techniques of the present disclosure, or that is capable of storing, encoding or carrying data structures used by or associated with such instructions. Non-limiting machine readable medium examples may include solid-state memories, and optical and magnetic media. Specific examples of machine readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 724 may further be transmitted or received over a communications network 726 using a transmission medium via the network interface device 720 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, IEEE 802.16 family of standards known as WiMax®), IEEE 802.15.4 family of standards, peer-to-peer (P2P) networks, among others. In an example, the network interface device 720 may include one or more physical jacks (e.g., Ethernet, coaxial, or phone jacks) or one or more antennas to connect to the communications network 726. In an example, the network interface device 720 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 700, and includes digital or analog communications signals or other intangible medium to facilitate communication of such software.

VARIOUS NOTES & EXAMPLES

Each of these non-limiting examples may stand on its own, or may be combined in various permutations or combinations with one or more of the other examples.

Example 1 is a method for determining a personalized gas level exposure, the method comprising: receiving, at a wearable device, a plurality of gas level measurements for a gas level; determining, using the plurality of gas level measurements, a five-minute average gas level; in response to determining that the five-minute average gas level exceeds an instantaneous exposure threshold, issuing a dangerous exposure alert at the wearable device; determining, from the plurality of gas level measurements, a rate of change for the gas level; and in response to etermining that the rate of change indicates the gas level is decreasing, disabling the dangerous exposure alert.

In Example 2, the subject matter of Example 1 optionally includes, wherein the rate of change indicates that the gas level is decreasing when the rate of change is negative and exceeds a slope threshold.

In Example 3, the subject matter of any one or more of Examples 1-2 optionally include, wherein the plurality of gas level measurements are made by a sensor of the wearable device.

In Example 4, the subject matter of any one or more of Examples 1-3 optionally include, wherein the gas level is a level of Carbon Monoxide gas.

In Example 5, the subject matter of any one or more of Examples 1-4 optionally include, further comprising, in response to determining that the five-minute average gas level falls below the instantaneous exposure threshold, indicating the gas level is at a safe level.

In Example 6, the subject matter of any one or more of Examples 1-5 optionally include, further comprising: determining, using the plurality of gas level measurements, a fifteen-minute average gas level; and in response to determining that the fifteen-minute average gas level exceeds an acute exposure threshold, issuing an acute alert at the wearable device.

In Example 7, the subject matter of Example 6 optionally includes, further comprising, when the five-minute average gas level exceeds the instantaneous exposure threshold, and the fifteen-minute average gas level exceeds the acute exposure threshold, issuing the dangerous exposure alert and not the acute alert.

In Example 8, the subject matter of any one or more of Examples 6-7 optionally include, further comprising disabling the acute alert when iterating the method results in the fifteen-minute average gas level exceeding the acute exposure threshold for twenty minutes.

In Example 9, the subject matter of any one or more of Examples 1-8 optionally include, further comprising: determining, using the plurality of gas level measurements, a set of twenty-four-hour average gas levels; and in response to determining that a minimum number of the set of twenty-four-hour average gas levels exceed a daily exposure threshold, issuing a chronic exposure alert at the wearable device.

In Example 10, the subject matter of Example 9 optionally includes, wherein the set of twenty-four-hour average gas levels includes seven twenty-four-hour average gas levels and wherein the minimum number is three.

In Example 11, the subject matter of any one or more of Examples 1-10 optionally include, further comprising: in response to a hardware button being pressed, determining, using the plurality of gas level measurements, a fifteen-minute average gas level; and determining where the fifteen-minute average gas level falls within a range.

In Example 12, the subject matter of Example 11 optionally includes, further comprising when the fifteen-minute average gas level falls in a lowest section of the range, indicating the gas level is at a safe level.

In Example 13, the subject matter of any one or more of Examples 11-12 optionally include, further comprising when the fifteen-minute average gas level falls in a middle section of the range, issuing a moderate gas level alert.

In Example 14, the subject matter of any one or more of Examples 11-13 optionally include, further comprising when the fifteen-minute average gas level falls in a highest section of the range, issuing a high gas level alert.

In Example 15, the subject matter of Example 14 optionally includes, wherein a minimum value of the highest section of the range is lower than the instantaneous exposure threshold.

Example 16 is at least one machine-readable medium including instructions for operation of a computing system, which when executed by a machine, cause the machine to perform operations of any of the methods of Examples 1-15.

Example 17 is an apparatus comprising means for performing any of the methods of Examples 1-15.

Example 18 is a wearable device for determining a personalized gas level exposure, the wearable device comprising: processing circuitry to: receive a plurality of gas level measurements for a gas level; determine, using the plurality of gas level measurements, a five-minute average gas level; in response to determining that the five-minute average gas level exceeds an instantaneous exposure threshold, issue a dangerous exposure alert; determine, from the plurality of gas level measurements, a rate of change for the gas level; and in response to determining that the rate of change indicates the gas level is decreasing, disable the dangerous exposure alert.

In Example 19, the subject matter of Example 18 optionally includes, wherein the rate of change indicates that the gas level is decreasing when the rate of change is negative and exceeds a slope threshold.

In Example 20, the subject matter of any one or more of Examples 18-19 optionally include, further comprising a sensor to measure the plurality of gas level measurements.

In Example 21, the subject matter of any one or more of Examples 18-20 optionally include, wherein the gas level is a level of Carbon Monoxide gas.

In Example 22, the subject matter of any one or more of Examples 18-21 optionally include, wherein, in response to determining that the five-minute average gas level falls below the instantaneous exposure threshold, the processing circuitry is to indicate the gas level is at a safe level.

In Example 23, the subject matter of any one or more of Examples 18-22 optionally include, wherein the processing circuitry is to: determine, using the plurality of gas level measurements, a fifteen-minute average gas level; and in response to determining that the fifteen-minute average gas level exceeds an acute exposure threshold, issue an acute alert.

In Example 24, the subject matter of Example 23 optionally includes, wherein, when the five-minute average gas level exceeds the instantaneous exposure threshold and the fifteen-minute average gas level exceeds the acute exposure threshold, the processing is to issue the dangerous exposure alert and not the acute alert.

In Example 25, the subject matter of any one or more of Examples 23-24 optionally include, further comprising a plurality of Light Emitting Diodes (LEDs), the LEDs including a red LED for the dangerous exposure alert and the acute alert, a yellow LED for the acute alert, and a green LED to indicate the gas level is at a safe level.

In Example 26, the subject matter of any one or more of Examples 18-25 optionally include, wherein the processing circuitry is to: determine, using the plurality of gas level measurements, a set of twenty-four-hour average gas levels; and in response to determining that a minimum number of the set of twenty-four-hour average gas levels exceed a daily exposure threshold, issue a chronic exposure alert.

In Example 27, the subject matter of Example 26 optionally includes, wherein the set of twenty-four-hour average gas levels includes seven twenty-four-hour average gas levels and wherein the minimum number is three.

In Example 28, the subject matter of any one or more of Examples 18-27 optionally include, wherein the processing circuitry is to: in response to a hardware button being pressed, determine, using the plurality of gas level measurements, a fifteen-minute average gas level; and determine where the fifteen-minute average gas level falls within a range.

In Example 29, the subject matter of Example 28 optionally includes, wherein when the fifteen-minute average gas level falls in a lowest section of the range, the processing circuitry is to indicate the gas level is at a safe level.

In Example 30, the subject matter of any one or more of Examples 28-29 optionally include, wherein when the fifteen-minute average gas level falls in a middle section of the range, the processing circuitry is to issue a moderate gas level alert.

In Example 31, the subject matter of any one or more of Examples 28-30 optionally include, wherein when the fifteen-minute average gas level falls in a highest section of the range, the processing circuitry is to issue a high gas level alert.

In Example 32, the subject matter of Example 31 optionally includes, wherein a minimum value of the highest section of the range is lower than the instantaneous exposure threshold.

Example 33 is at least one machine readable medium including instructions that, when executed, cause the machine to perform operations for determining a personalized gas level exposure, the operations comprising: receiving, at a wearable device, a plurality of gas level measurements for a gas level; determining, using the plurality of gas level measurements, a five-minute average gas level; in response to determining that the five-minute average gas level exceeds an instantaneous exposure threshold, issuing a dangerous exposure alert at the wearable device; determining, from the plurality of gas level measurements, a rate of change for the gas level; and in response to determining that the rate of change indicates the gas level is decreasing, disabling the dangerous exposure alert.

In Example 34, the subject matter of Example 33 optionally includes, wherein the rate of change indicates that the gas level is decreasing when the rate of change is negative and exceeds a slope threshold.

In Example 35, the subject matter of any one or more of Examples 33-34 optionally include, wherein the plurality of gas level measurements are made by a sensor of the wearable device.

In Example 36, the subject matter of any one or more of Examples 33-35 optionally include, wherein the gas level is a level of Carbon Monoxide gas.

In Example 37, the subject matter of any one or more of Examples 33-36 optionally include, further comprising, in response to determining that the five-minute average gas level falls below the instantaneous exposure threshold, indicating the gas level is at a safe level.

In Example 38, the subject matter of any one or more of Examples 33-37 optionally include, further comprising: determining, using the plurality of gas level measurements, a fifteen-minute average gas level; and in response to determining that the fifteen-minute average gas level exceeds an acute exposure threshold, issuing an acute alert at the wearable device.

In Example 39, the subject matter of Example 38 optionally includes, further comprising, when the five-minute average gas level exceeds the instantaneous exposure threshold, and the fifteen-minute average gas level exceeds the acute exposure threshold, issuing the dangerous exposure alert and not the acute alert.

In Example 40, the subject matter of any one or more of Examples 38-39 optionally include, wherein the dangerous exposure alert includes a first audio portion and the acute alert includes a second audio portion.

In Example 41, the subject matter of any one or more of Examples 33-40 optionally include, further comprising: determining, using the plurality of gas level measurements, a set of twenty-four-hour average gas levels; and in response to determining that a minimum number of the set of twenty-four-hour average gas levels exceed a daily exposure threshold, issuing a chronic exposure alert at the wearable device.

In Example 42, the subject matter of Example 41 optionally includes, wherein the set of twenty-four-hour average gas levels includes seven twenty-four-hour average gas levels and wherein the minimum number is three.

In Example 43, the subject matter of any one or more of Examples 33-42 optionally include, further comprising: in response to a hardware button being pressed, determining, using the plurality of gas level measurements, a fifteen-minute average gas level; and determining where the fifteen-minute average gas level falls within a range.

In Example 44, the subject matter of Example 43 optionally includes, further comprising when the fifteen-minute average gas level falls in a lowest section of the range, indicating the gas level is at a safe level.

In Example 45, the subject matter of any one or more of Examples 43-44 optionally include, further comprising when the fifteen-minute average gas level falls in a middle section of the range, issuing a moderate gas level alert.

In Example 46, the subject matter of any one or more of Examples 43-45 optionally include, further comprising when the fifteen-minute average gas level falls in a highest section of the range, issuing a high gas level alert.

In Example 47, the subject matter of Example 46 optionally includes, wherein a minimum value of the highest section of the range is lower than the instantaneous exposure threshold.

Example 48 is an apparatus for determining a personalized gas level exposure, the apparatus comprising: means for receiving, at a wearable device, a plurality of gas level measurements for a gas level; means for determining, using the plurality of gas level measurements, a five-minute average gas level; in response to determining that the five-minute average gas level exceeds an instantaneous exposure threshold, means for issuing a dangerous exposure alert at the wearable device; means for determining, from the plurality of gas level measurements, a rate of change for the gas level; and in response to determining that the rate of change indicates the gas level is decreasing, means for disabling the dangerous exposure alert.

In Example 49, the subject matter of Example 48 optionally includes, wherein the rate of change indicates that the gas level is decreasing when the rate of change is negative and exceeds a slope threshold.

In Example 50, the subject matter of any one or more of Examples 48-49 optionally include, wherein the plurality of gas level measurements are made by a sensor of the wearable device.

In Example 51, the subject matter of any one or more of Examples 48-50 optionally include, wherein the gas level is a level of Carbon Monoxide gas.

In Example 52, the subject matter of any one or more of Examples 48-51 optionally include, further comprising, in response to determining that the five-minute average gas level falls below the instantaneous exposure threshold, means for indicating the gas level is at a safe level.

In Example 53, the subject matter of any one or more of Examples 48-52 optionally include, further comprising: means for determining, using the plurality of gas level measurements, a fifteen-minute average gas level; and in response to determining that the fifteen-minute average gas level exceeds an acute exposure threshold, means for issuing an acute alert at the wearable device.

In Example 54, the subject matter of Example 53 optionally includes, further comprising, when the five-minute average gas level exceeds the instantaneous exposure threshold, and the fifteen-minute average gas level exceeds the acute exposure threshold, means for issuing the dangerous exposure alert and not the acute alert.

In Example 55, the subject matter of any one or more of Examples 53-54 optionally include, wherein the dangerous exposure alert includes a first audio portion and the acute alert includes a second audio portion.

In Example 56, the subject matter of any one or more of Examples 48-55 optionally include, further comprising: means for determining, using the plurality of gas level measurements, a set of twenty-four-hour average gas levels; and in response to determining that a minimum number of the set of twenty-four-hour average gas levels exceed a daily exposure threshold, means for issuing a chronic exposure alert at the wearable device.

In Example 57, the subject matter of Example 56 optionally includes, wherein the set of twenty-four-hour average gas levels includes seven twenty-four-hour average gas levels and wherein the minimum number is three.

In Example 58, the subject matter of any one or more of Examples 48-57 optionally include, further comprising: in response to a hardware button being pressed, means for determining, using the plurality of gas level measurements, a fifteen-minute average gas level; and means for determining where the fifteen-minute average gas level falls within a range.

In Example 59, the subject matter of Example 58 optionally includes, further comprising when the fifteen-minute average gas level falls in a lowest section of the range, means for indicating the gas level is at a safe level.

In Example 60, the subject matter of any one or more of Examples 58-59 optionally include, further comprising when the fifteen-minute average gas level falls in a middle section of the range, means for issuing a moderate gas level alert.

In Example 61, the subject matter of any one or more of Examples 58-60 optionally include, further comprising when the fifteen-minute average gas level falls in a highest section of the range, means for issuing a high gas level alert.

In Example 62, the subject matter of Example 61 optionally includes, wherein a minimum value of the highest section of the range is lower than the instantaneous exposure threshold.

Method examples described herein may be machine or computer-implemented at least in part. Some examples may include a computer-readable medium or machine-readable medium encoded with instructions operable to configure an electronic device to perform methods as described in the above examples. An implementation of such methods may include code, such as microcode, assembly language code, a higher-level language code, or the like. Such code may include computer readable instructions for performing various methods. The code may form portions of computer program products. Further, in an example, the code may be tangibly stored on one or more volatile, non-transitory, or non-volatile tangible computer-readable media, such as during execution or at other times. Examples of these tangible computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

What is claimed is:

1. A wearable device for determining a personalized gas level exposure, the wearable device comprising:
   processing circuitry to:
      receive a plurality of gas level measurements for a gas level;
      determine, using the plurality of gas level measurements, a first time period average gas level;
      in response to determining that the first time period average gas level exceeds an instantaneous exposure threshold, issue a dangerous exposure alert;
      determine, from the plurality of gas level measurements, a rate of change for the gas level; and
      in response to determining that the rate of change indicates the gas level is decreasing, disable the dangerous exposure alert.

2. The wearable device of claim 1, further comprising a sensor to measure the plurality of gas level measurements.

3. The wearable device of claim 1, wherein the processing circuitry is to:
   determine, using the plurality of gas level measurements, a fifteen-minute average gas level; and
   in response to determining that the fifteen-minute average gas level exceeds an acute exposure threshold, issue an acute alert.

4. The wearable device of claim 3, wherein, when the first time period average gas level is a five-minute average gas level and exceeds the instantaneous exposure threshold and the fifteen-minute average gas level exceeds the acute exposure threshold, the processing is to issue the dangerous exposure alert and not the acute alert.

5. The wearable device of claim 3, further comprising a plurality of Light Emitting Diodes (LEDs), the LEDs including a red LED for the dangerous exposure alert and the acute alert, a yellow LED for the acute alert, and a green LED to indicate the gas level is at a safe level.

6. A method for determining a personalized gas level exposure, the method comprising:
    receiving, at a wearable device, a plurality of gas level measurements for a gas level;
    determining, using the plurality of gas level measurements, a five-minute average gas level;
    in response to determining that the five-minute average gas level exceeds an instantaneous exposure threshold, issuing a dangerous exposure alert at the wearable device;
    determining, from the plurality of gas level measurements, a rate of change for the gas level; and
    in response to determining that the rate of change indicates the gas level is decreasing, disabling the dangerous exposure alert.

7. The method of claim 6, wherein the rate of change indicates that the gas level is decreasing when the rate of change is negative and exceeds a slope threshold.

8. The method of claim 6, wherein the plurality of gas level measurements are made by a sensor of the wearable device.

9. The method of claim 6, wherein the gas level is a level of carbon monoxide gas.

10. The method of claim 6, further comprising, in response to determining that the five-minute average gas level falls below the instantaneous exposure threshold, indicating the gas level is at a safe level.

11. The method of claim 6, further comprising:
    determining, using the plurality of gas level measurements, a fifteen-minute average gas level; and
    in response to determining that the fifteen-minute average gas level exceeds an acute exposure threshold, issuing an acute alert at the wearable device.

12. The method of claim 11, further comprising, when the five-minute average gas level exceeds the instantaneous exposure threshold, and the fifteen-minute average gas level exceeds the acute exposure threshold, issuing the dangerous exposure alert and not the acute alert.

13. The method of claim 11, further comprising disabling the acute alert when iterating the method results in the fifteen-minute average gas level exceeding the acute exposure threshold for 20 minutes.

14. The method of claim 6, further comprising:
    determining, using the plurality of gas level measurements, a set of twenty-four-hour average gas levels; and
    in response to determining that a minimum number of the set of twenty-four-hour average gas levels exceed a daily exposure threshold, issuing a chronic exposure alert at the wearable device.

15. The method of claim 14, wherein the set of twenty-four-hour average gas levels includes seven twenty-four-hour average gas levels and wherein the minimum number is three.

16. The method of claim 6, further comprising:
    in response to a hardware button being pressed, determining, using the plurality of gas level measurements, a fifteen-minute average gas level; and
    determining where the fifteen-minute average gas level falls within a range.

17. The method of claim 16, further comprising when the fifteen-minute average gas level falls in a lowest section of the range, indicating the gas level is at a safe level.

18. The method of claim 16, further comprising when the fifteen-minute average gas level falls in a middle section of the range, issuing a moderate gas level alert.

19. The method of claim 16, further comprising when the fifteen-minute average gas level falls in a highest section of the range, issuing a high gas level alert.

20. The method of claim 19, wherein a minimum value of the highest section of the range is lower than the instantaneous exposure threshold.

21. At least one non-transitory machine readable medium including instructions that, when executed, cause the machine to perform operations for determining a personalized gas level exposure, the operations comprising:
    receiving, at a wearable device, a plurality of gas level measurements for a gas level;
    determining, using the plurality of gas level measurements, a first time period average gas level;
    in response to determining that the first time period average gas level exceeds an instantaneous exposure threshold, issuing a dangerous exposure alert at the wearable device;
    determining, from the plurality of gas level measurements, a rate of change for the gas level; and
    in response to determining that the rate of change indicates the gas level is decreasing, disabling the dangerous exposure alert.

22. The at least one machine readable medium of claim 21, further comprising:
    determining, using the plurality of gas level measurements, a fifteen-minute average gas level; and
    in response to determining that the fifteen-minute average gas level exceeds an acute exposure threshold, issuing an acute alert at the wearable device.

23. The at least one machine readable medium of claim 22, wherein the dangerous exposure alert includes a first audio portion and the acute alert includes a second audio portion.

* * * * *